United States Patent [19]
Corin et al.

[11] Patent Number: 5,667,507
[45] Date of Patent: Sep. 16, 1997

[54] COMPRESSION LOCKING VARIABLE LENGTH CROSS-LINK DEVICE FOR USE WITH DUAL ROD APPARATUS

[75] Inventors: James D. Corin, Englewood, Colo.; Joseph P. Errico, Far Hills; James D. Ralph, Oakland, both of N.J.

[73] Assignee: Fastenetix, LLC, Summit, N.J.

[21] Appl. No.: 567,144

[22] Filed: Dec. 4, 1995

[51] Int. Cl.⁶ ................................................. A61B 17/56
[52] U.S. Cl. .............................. 606/61; 606/63; 606/64; 606/73
[58] Field of Search ................................ 606/61, 63, 64, 606/72, 73

[56] References Cited

U.S. PATENT DOCUMENTS

| | | | |
|---|---|---|---|
| 4,085,744 | 4/1978 | Lewis et al. | 606/61 |
| 5,147,360 | 9/1992 | Dubousset | 606/61 |
| 5,439,463 | 8/1995 | Lin | 606/61 |

Primary Examiner—Michael Buiz
Assistant Examiner—Mark S. Leonardo
Attorney, Agent, or Firm—Joseph P. Errico, Esq.

[57] ABSTRACT

A compression locking variable length cross-link device having a pair of rod hooking elements, each having rod securing and flat coupling ends. The flat coupling ends are slidably coupled to one another for selective locking to one another independent of the relative separation of the rod securing ends. Each hooking element has a curvate end formed from flat material which has been shaped into a hook conformation to cup the lateral outside surface of a corresponding rod. A set screw positioned through a hole in the top of the curved end locks the curvate end to the rod. In a first embodiment, one (a first) rod hooking element has a narrow flat end having a knurled top surface. The corresponding flat end of the other (second) element is wider, has a knurled undersurface, and has a hole therethrough for receiving a post. The post has a transverse passageway through it for slidably receiving the narrow flat portion of the first element, and an upper portion which is threaded. The threaded upper portion is positioned in the hole of the flat end of the second element. Tightening of a top locking nut causes the two knurled portions of the flat ends to compression lock together. In a second embodiment, the undersurface of the flat end of first element is knurled. The second element has a thickened corresponding end, having a flat passageway through it for slidably receiving the flat end of the first element. A set screw may then be engaged through a hole in the top of the thickened portion to compress and lock the two together.

12 Claims, 10 Drawing Sheets

COMPRESSION LOCKING VARIABLE LENGTH CROSS-LINK DEVICE FOR USE WITH DUAL ROD APPARATUS

BACKGROUND OF THE INVENTION

1. Field of the Invention

This invention relates generally to a mechanical cross-link device for use with dual rod orthopaedic implant apparatus. More particularly, this invention relates to a novel device which is fixed to each rod dual rod implant apparatus, and maintains and enhances the rigidity of the apparatus along a direction which is substantially transverse to the customary vertical orientation of the rods.

2. Discussion of the Prior Art

The bones and connective tissue of an adult human spinal column consist of an upper portion (the cervical, thoracic, and lumbar regions) having more than 20 discrete bones, and a lower portion which consists of the sacral bone and the coccygeal bodies. The bones of the upper portion are generally similar in shape, as will be more fully described hereinbelow with respect to FIGS. 1, 2 and 3. For the purpose of describing this invention, the sacral bone shall be distinguished from the spinal column; the spinal column, therefore, comprising for the purposes of this description, only the cervical, thoracic, and lumbar vertebrae.

Figure 1:
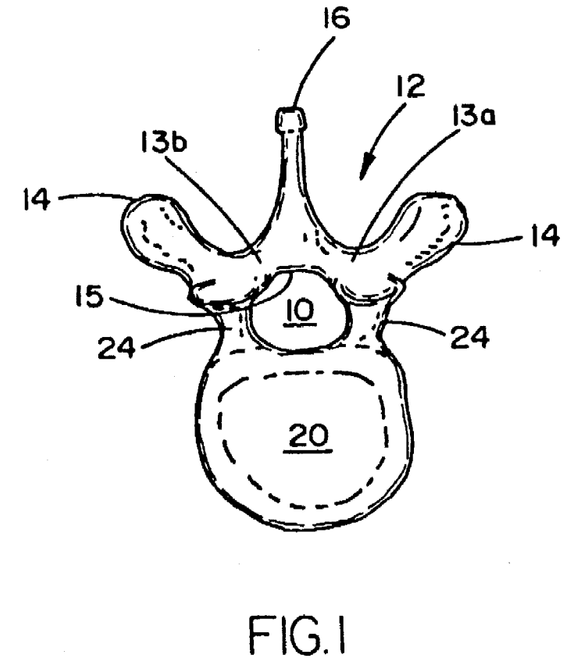
FIG. 1 is a top view of a vertebra of the human spine.
Figure 2:
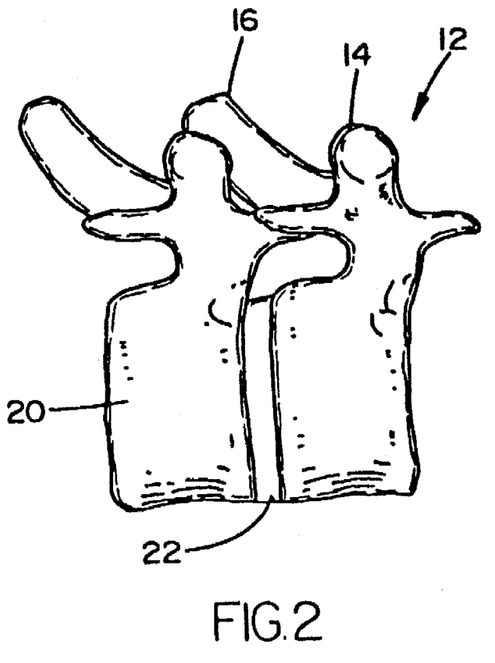
FIG. 2 is a side view of a sequence of vertebrae of the human spine.
Figure 3:
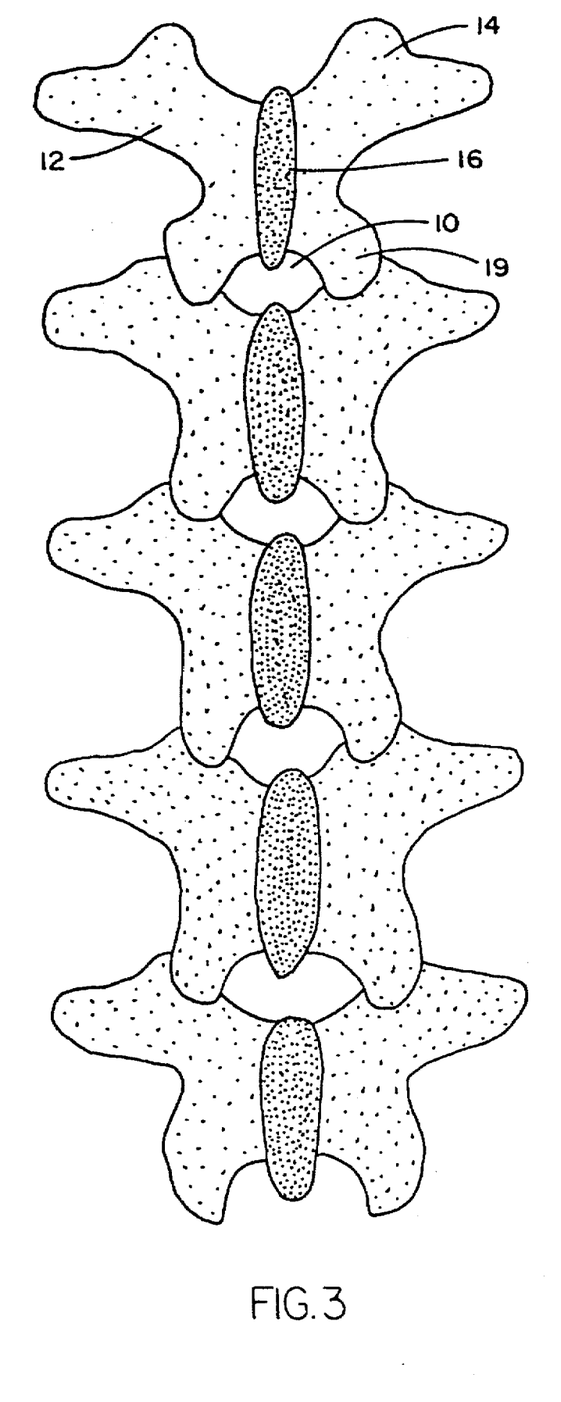
FIG. 3 is a posterior view of a sequence of vertebrae of the human spine.

The vertebrae vary in size, but are each similarly coupled to adjacent bones by a tri-joint complex. The tri-joint complex consists of an anterior disc and the two posterior facet joints, the anterior discs of adjacent bones being cushioned by cartilage spacers referred to as intervertebral discs. Referring now to FIGS. 1, 2 and 3, top, lateral, and posterior views of a typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a, 13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatuses generally include cross-linking devices which couple the rods together transverse to the axis (vertical axis) of the apparatuses.

Figure 4:
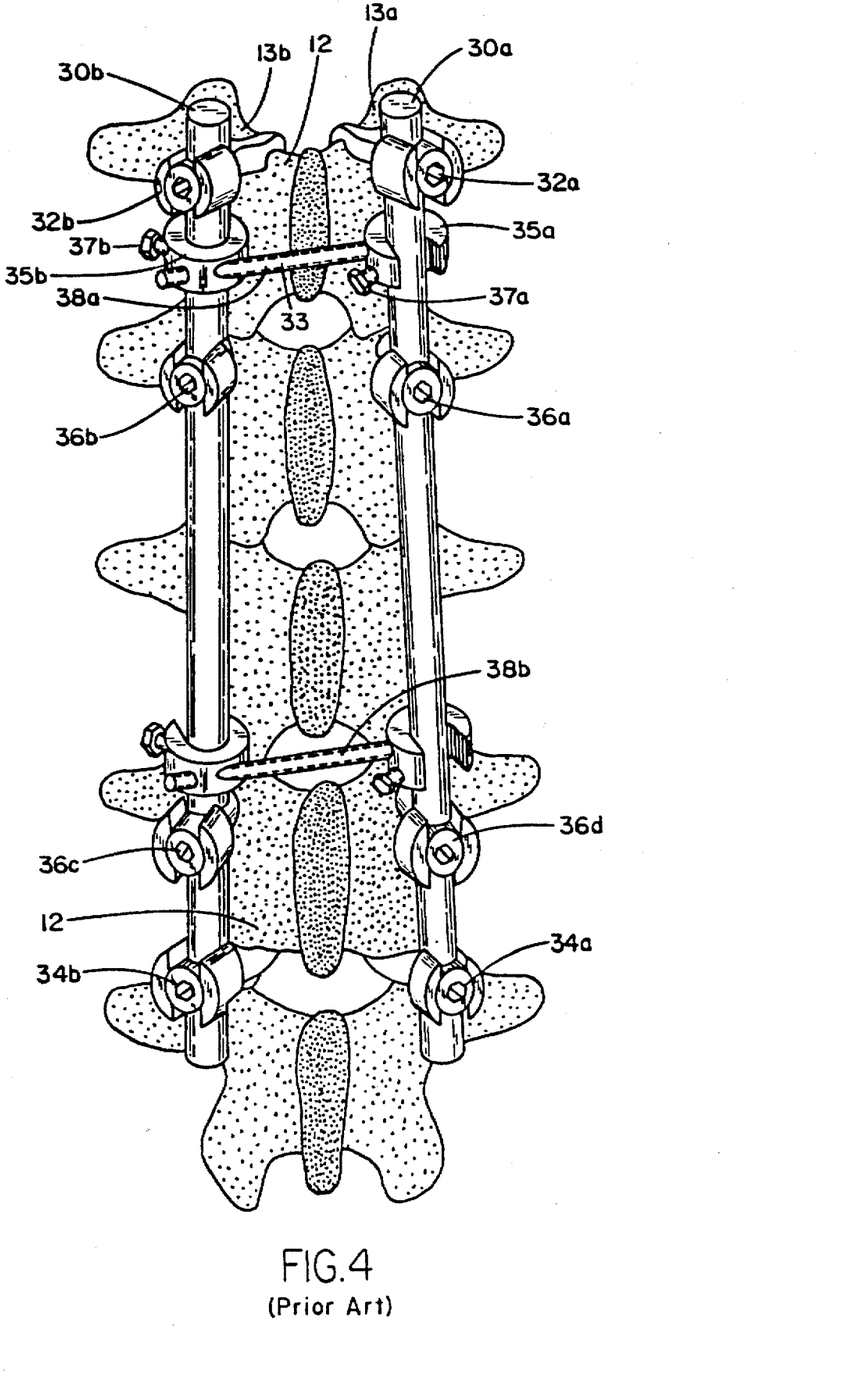
FIG. 4 is a posterior view of a dual rod apparatus of a prior art instrumentation as set forth in U.S. Pat. No. 5,005,562 to Cotrel, including cross-link devices.

Referring now to FIG. 4, U.S. Pat. No. 5,005,562 to Cotrel teaches such a dual rod apparatus which includes a pair of rods 30a,30b, which are each coupled to the spine via hooks 32a,34a and 32b,34b, respectively, as well as pedicle screws 36a,36d and 36b,36c, respectively. The rods 30a,30b are further stabilized by cross-link devices 38a,38b. These cross-link devices 38a,38b each include a pair of U-shaped gripping element 35a,35b which may receive the rod 30a, 30b respectively. Each of the gripping elements includes a first threaded hole which extends from the outer lateral surface into the inner surface of the U-shaped rod receiving region. The gripping elements 35a,35b are fixed to the rods 30a,30b by set screws 37a,37b which are positioned in the first holes such that tightening of the set screws locks the rod 30a,30b in the gripping element. The gripping elements 35a,35b are coupled together by a threaded rod 33 which permits the gripping elements to be selectively spread or brought closer together, in accordance with the relative position of the rods 30a,30b. The threaded rod 33 extends through a second set of threaded holes in the gripping elements 35a,35b.

The bulkiness of each of the gripping elements 35a,35b, required so that it may receive the threaded rod 33, is difficult for the surgeon to use easily under operative conditions. The size of the gripping elements, and the relative position of the set screws often cause substantial difficulty with respect to the tightening of same because of their positions relative to the operative access. This bulkiness also reduces available bone graft surface area, which is critical for a successful fusion and long term immobilization. In addition, in order for a surgeon to selectively vary the spread of the gripping elements 35a,35b, one of the gripping elements must be rotated relative to the other, thus requiring the cross-link to be removed (loosening the set screws and withdrawing the device entirely from the operative site). This is particularly burdensome with respect to providing the surgeon with the ability to apply an inward force to the rods 30a,30b as the spread may not be varied in situ.

It is therefore, a principal object of the present invention to provide a new and novel cross-link device which provides a less bulky profile, therein providing increased area for bone grafting.

It is also an object of the present invention to provide a cross-link device which provides the surgeon with the ability to lock the device to the rods more easily than prior cross-link devices.

It is also, therefore, an object of the present invention to provide a cross-link device which provides the surgeon with the ability to vary the spread of the rod gripping portions in situ, so that in doing so, the surgeon is not required to withdraw the device from the patient.

It is correspondingly an object of the present invention to provide a cross-link device which permits the surgeon to use the variable spread of the device to impart an inward force relative to the two rods, which is a desirable feature for the purposes of enhanced rotational stability.

Other objects of the present invention not explicitly stated will be set forth, and will be more clearly understood, in conjunction with the descriptions of the preferred embodiments disclosed hereafter.

SUMMARY OF THE INVENTION

The preceding objects of the invention are achieved by the present invention which is a compression locking variable length cross-link device which may be affixed to the rods of a dual rod implant apparatus. The present invention may be practiced in a variety of different embodiments; the several enclosed herein being representative of preferred ones of the invention.

Each of the embodiments described herein includes a pair of rod hooking elements formed of a substantially flat rigid material, for example medical grade steel or titanium. Each of the pair of rod hooking elements has a first end which is curvate so as to receive therein and/or seat against and hook to the lateral outside surface of a first rod of a dual rod apparatus, and a second flat end. With respect to the curvate ends of the rod hooking elements, each includes a through hole for receiving a set screw. The set screw positioned therein is designed to be threadably tightened downward onto the rod against which the first end is seated, therein locking the rod and element together.

More particularly with respect to the first embodiment, the two rod hooking elements are designed to be coupled together by a threaded post, which shall be described more fully hereinafter. The first of the two rod hooking elements comprises a flat end which is narrowed to a width which is substantially less than the width of the flat material of which the rod securing end is formed (the thickness and corresponding structural strength of the flat end is desirably the same as that of the rod securing end). In addition, it is desirable for the top surface of this flat end to have a grooved or roughened conformation, for example a diamond knurling.

With respect to the other of the rod hooking elements of the pair which comprise this first embodiment, as stated above, the rod securing end thereof has a curvate shape for receiving therein and/or seating against lateral outside surface the second rod of the dual rod apparatus. This curvate end includes a through hole for receiving a set screw for locking the rod to the curvate shaped end. The flat end of this second rod hooking element is substantially wider than the flat end of the first element; being approximately as wide as the rod securing end. This flat end comprises a through hole which is wide enough to receive the above-introduced, threaded post, which is described more fully hereinbelow. In addition, the undersurface of the flat end of the second rod securing element is correspondingly roughened with, for example a diamond knurl.

The coupling of these two rod hooking elements is achieved by the incorporation of a threaded post. This threaded post is generally cylindrical and comprises a widened base, an intermediate portion having a passageway defined therethrough which is transverse to the axis of the post, and a threaded upper portion. The flat end of the first rod hooking element is inserted through the passageway, such that the knurled upper surface of the flat end is oriented upward. The threaded upper portion of the post is positioned through the hole in the flat portion of the second rod hooking element such that the knurled lower and upper surfaces of the flat ends of the first and second rod hooking elements contact on another. A top locking nut is then threaded onto the upper portion of the post. Prior to the tightening of the nut, the flat end of the first element may slide relative to the flat portion of the second, so that the rod securing portions may be spread or drawn together in accordance with the positioning of the rods. Tightening of the nut down onto the top surface of the second flat portion causes the post to be drawn upwards until the roughened surfaces of the first and second flat portions seat and lock to one another under the compressive force.

In a second embodiment of the present invention, the first rod hooking element comprises substantially the same shape and features as the first element of the first embodiment, but for the removal of a surface roughening on the top surface of the flat portion and a similar roughening of the bottom surface thereof. More particularly, the rod hooking element includes a curvate rod securing end, formed of a flat material, for example medical grade steel or titanium, which has been curved into a hook shape for receiving therein, or seating against a lateral outside surface of one of the rods of a dual rod apparatus. The curvate rod securing end further includes a through hole for receiving a set screw which is used to lock the element to the rod. The other end of the element comprises a narrowed flat portion having a roughened bottom surface, said surface having, for example, a diamond knurl.

The second rod hooking element of this second embodiment also includes the equivalent curvate rod securing end, however, the flat end thereof comprises a thickened portion at its extreme end, the thickened portion having a flat passageway therethrough. More specifically, the extreme end of the flat portion has a width and thickness which is substantially greater than the flat end of the first element of this embodiment, and substantially thicker than the remainder of the element. This thickened section may be vertically divided into a bottom, an intermediate, and an upper part. The intermediate part comprises a flat passageway, through which the flat portion of the first element may be inserted. The bottom part, which is integrally mounted to the thinner remainder of the flat portion, has a top surface (which is correspondingly contiguous and co-planar with the top surface of the remaining section of the flat portion of the second element) which is roughened, such as with a diamond knurl. The upper part of the thickened section is a substantially flat material having a through hole which extends from a center of the top surface of the upper part to the top of the flat passageway (the intermediate portion). This through hole is designed to receive a set screw, much like the set screws used in conjunction with the rod securing ends to lock the elements to their respective rods. This set screw applies a downward locking force onto the top of the narrow flat portion of the first element, compressing the roughened surfaces of each flat portions together and locking the elements together. It is understood that prior to the tightening of the set screw, the first and second elements may be spread or brought together to the extent provided by the respective lengths of the flat portions, so that each of the rod securing portions may be seated snugly against its corresponding rod independent of the mutual separation of the pair.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 5:
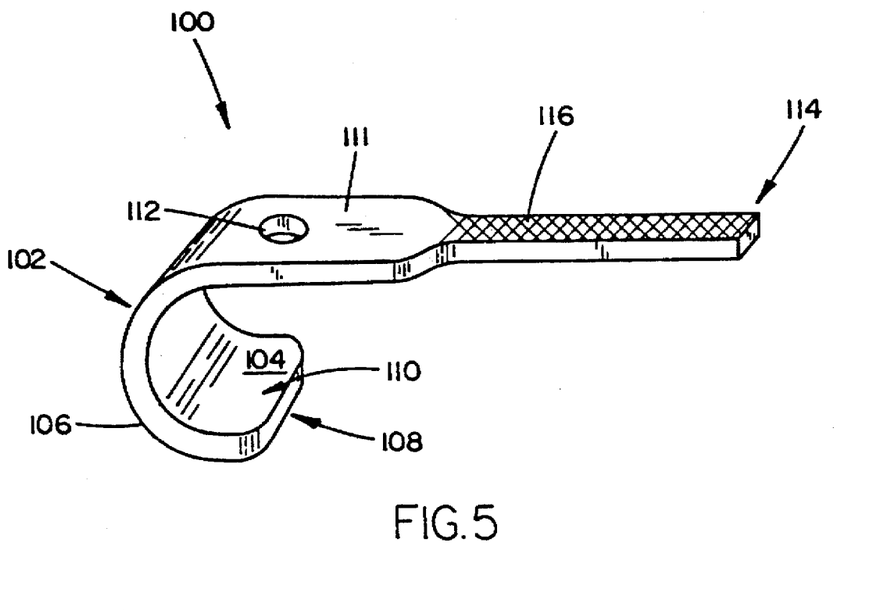
FIG. 5 is a side perspective view of a first rod hooking element which is an aspect of the present invention.

Referring now to FIG. 5, a first rod hooking element 100 of the first embodiment of the present invention is provided in a side perspective view. As with all elements of this invention, the material of which this rod hooking element may comprise a high strength material, for example medical grade steel or titanium compounds, which has been found ideally suited for implantation into the human body. The rod hooking element 100 shown in FIG. 5 is specifically formed of a thin and flat sheet of metal, the first end 102 of which has been curved to the shape of a hook. The hook has a semi-circular curvature defined by an inner surface 104 and an outer surface 106. The lower portion 108 of the semi-circular hook extends tangentially for a small distance, parallel to the remainder of the element. The curve is semi-circular so that it can cup and hook to the lateral outside surface of a first rod of a dual rod apparatus. The lower extending portion 108 provides addition locking surface 110 against which the rod may be compressed by a locking means described more fully below.

The top portion 111 of the first end 102 comprises a through hole 112 which is threaded and extends from a point on the top surface of the first end 102 which is to adjacent to the initial curvature of the hook portion 102 to the underside of the same. Inasmuch as a set screw (set forth with respect to FIG. 6) is to be directed therethrough to lock the element 100, and more specifically the first end 102 thereof, to a rod of the implant assembly, the through hole 112 may be angled such that the insertion and subsequent tightening of the set screw drives same toward the inner surface 104 of the hook. Such a preset angle of the through hole orientation enhances the locking strength of the set screw by increasing the cupping surface against which the rod is crushed.

The other end 114 of the rod hooking element comprises a narrowed and flat portion which has a width which is substantially reduced as compared with that of the first rod securing end 102. The thickness and corresponding structural strength of this second end 114 is, however, desirably the same as that of the rod securing end. The top surface 116 of this second narrowed end 114 includes a roughening, for example a diamond knurling, which provides a greater coefficient of static friction to it; this enhanced friction coefficient being desirable for the purposes of compression locking this top surface against another surface.

Figure 6:
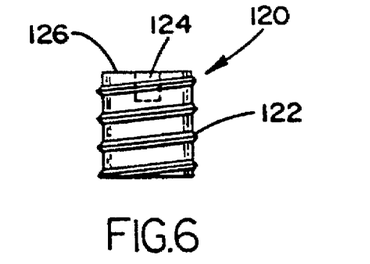
FIG. 6 is a side view of a set screw which is another aspect of the present invention.

Referring now to FIG. 6, a side view of the set screw 120 which is used to lock the rod to the first end 102 of the rod hooking element 100 (and for applying a compression pressure as described in regards to the second embodiment set forth herein) is provided. The set screw 120 comprises a surface threading 122 which is ideally suited to the threading of the through hole 112. The screw 120 further includes a recess 124 in the top 126 thereof, the recess having an internal conformation which may be engaged by a suitable tool for applying a torsional force thereto, for example a slot for a screwdriver or a hexagonally angled interior wall for an allen wrench.

Figure 7:
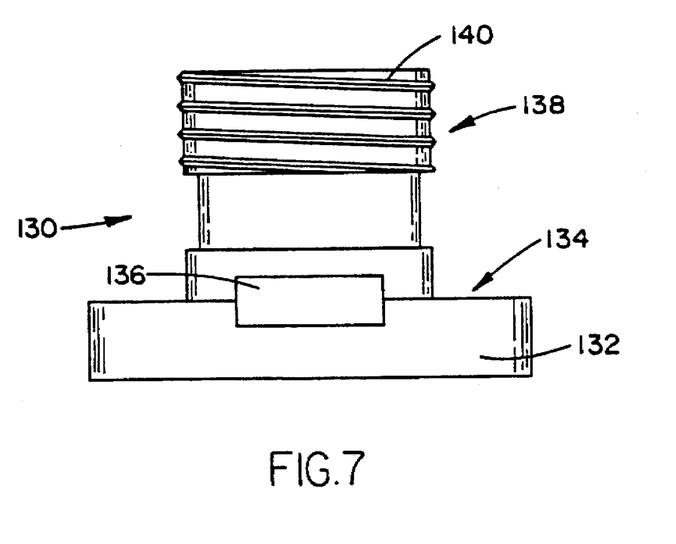
FIG. 7 is a side view of a post which is also used in conjunction with an embodiment of the present invention.
Figure 8:
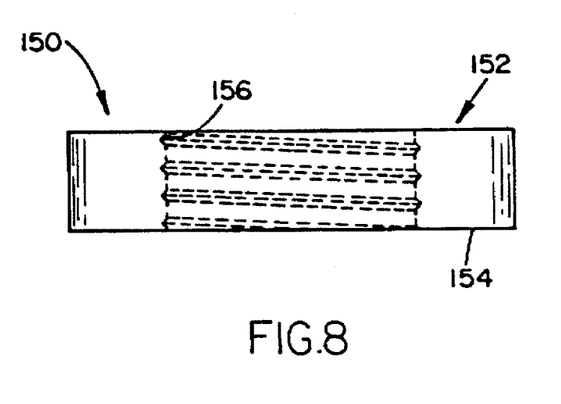
FIG. 8 is a side view of a top locking nut which threadably mates to an upper portion of the post of FIG. 7.

Referring now to FIGS. 7 and 8, side view of the post 130 and the top locking nut 150, which together provides the compression coupling of the elements of this embodiment is provided. Specifically referring to FIG. 7, the post 130 has a generally cylindrical shape. The base 132 of the post is wider than the upper portions, forming an annular flange 134. This annular flange 134 may include a surface roughening so that it may have an enhanced gripping strength against any surface against which it might be compressed.

The upper portion of the base 132, and the lower portion of the intermediate section of the post 130 includes a passageway 136 which extends transverse to the axis of the post, and which has a substantially rectangular cross-section. This passageway 136 is ideally suited for slidably receiving therethrough the flat extending end 114 of the first rod hooking element 100 (see FIG. 5). The height of the passageway 136 is desirably slightly larger than the thickness of the flat extending end 114, but the width of the passageway 136 is desirably the same. These dimensions eliminate any rotation or angulation of the first rod hooking element 100 relative to the post 130.

The upper portion 138 of the post 130 extends upward from the passageway 136 and the intermediate portion, and comprise a threading 140 which is ideally suited for receiving thereon a top locking nut. With reference to FIG. 8, the top locking nut 150 comprises a top surface 152 and a bottom surface 154, and an interior threading 156.

Figure 9:
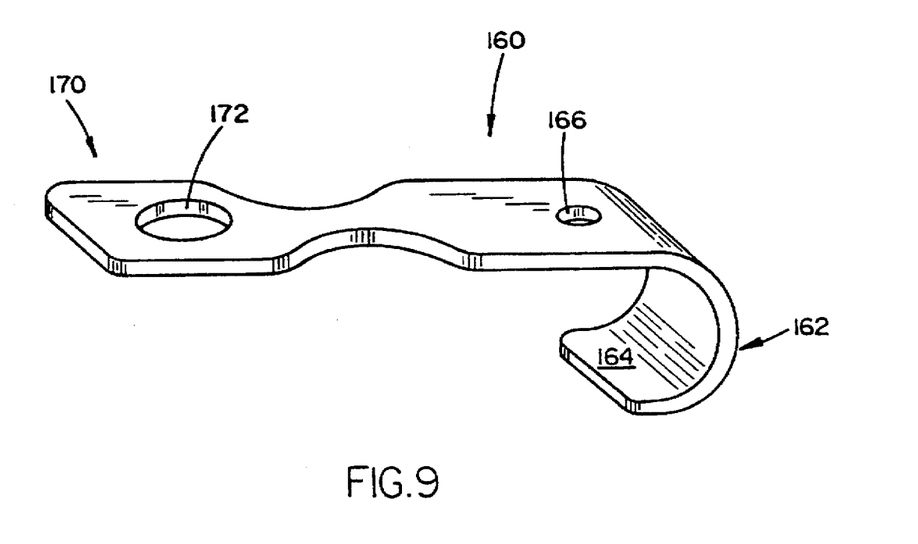
FIG. 9 is a side perspective view of a second rod hooking element which is an aspect of the present invention.

Referring now to FIG. 9, the second rod hooking element 160 is provided in a side perspective view. The second element 160 includes a rod securing end 162 which is substantially similar to the equivalent feature of the first element 100. More specifically, the rod securing end 162 thereof has a curvate shape and an interior surface 164 for seating against lateral outside surface the second rod of the dual rod apparatus. This curvate end 162 includes a through hole 166 for receiving a set screw 120 for locking the rod to the curvate shaped end.

The other end 170 of this second rod hooking element 160 is substantially wider than the flat end 114 of the first element 100. The undersurface of this end 170 (not shown) may comprise a surface roughening similar to, or at least ideally suited for engaging, the roughened top surface 116 of the first element. This end 170 comprises a through hole 172 which has a width equal to or greater than the width of the upper threaded portion 136, and the intermediate portions of the post 130.

Figure 10:
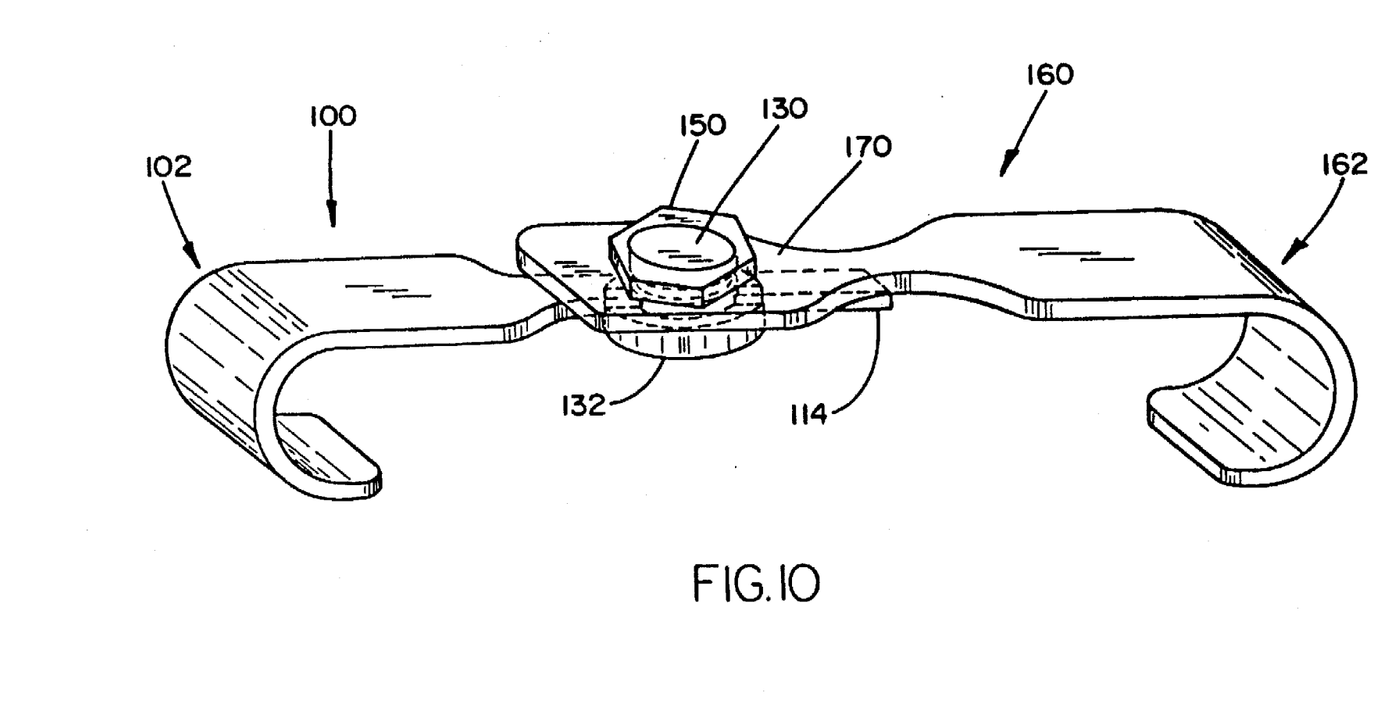
FIG. 10 is a side perspective view of a fully assembled embodiment of the present invention comprising all of the elements illustrated in FIGS. 5-9.

With reference now to FIG. 10, in which a fully assembled first embodiment of the present invention is provided in a side perspective view, the method of assembly and the locking of the elements is described. First the proper site for the fixation of the dual rod cross-link device is identified by the surgeon. The site should provide enough space along the rods for engagement of rod securing ends 102 and 162. Once this site is found, and the space separating the rods is cleared of all obstacles (for example, the spinous process) the narrow and flat extending portion 114 of the first element 100 is inserted into the passageway 136 of the post 130, such that the roughened top surface 116 of the extending portion 114 is oriented in the direction of the upper section 138 of the post 130.

Once the flat extending portion 114 has been inserted, the upper section 138 of the post 130 is inserted through the hole 172 in the rod coupling flat extending portion 170 of the second element 160. The post 130 is inserted upwardly so that the top locking nut 150, and more specifically the threads 156 thereof, may engage the threads 140 of the upper portion 138. Initial tightening of the nut 150 downward on the post 130 causes the bottom surface 154 of the nut to seat against the top surface of the flat extending portion 160. At this point the flat extending portion 114 of the first element 100 remains slidable relative to both the post 130 and the second element 160. The rod securing portions 102 and 162 may be selectively spread or drawn together by an amount determined solely by the length of the flat extending portion 114 of the first element 100. (In addition, it may be understood that inasmuch as the post 130 is not secured to the through hole 172, the post may be rotated, thus angulating the first and second elements 100 and 160 relative to one another from their co-linear orientation. While minimal rotation is desired, so as to maximize the contact surfaces of the extending portions 114 and 170, slight angulations may be useful in cases wherein the rods are not locally parallel, but comprise a small convergence or divergence.)

Continued tightening of the nut 150, however, causes the post 130 to be drawn upwards through the hole 172, thereby causing the intermediate section, and the passageway 136 thereof to be similarly drawn upwards. In doing so, the roughened top surface 116 of the narrowed flat extending portion 114 is compressed against the roughened lower surface of the second flat extending portion 170, locking the two together and locking the length of the cross-link.

Once the length of the cross-link is been set, the set screws 120 may be tightened down, thereby locking the element 100 and 160 to the rods themselves.

Figure 11:
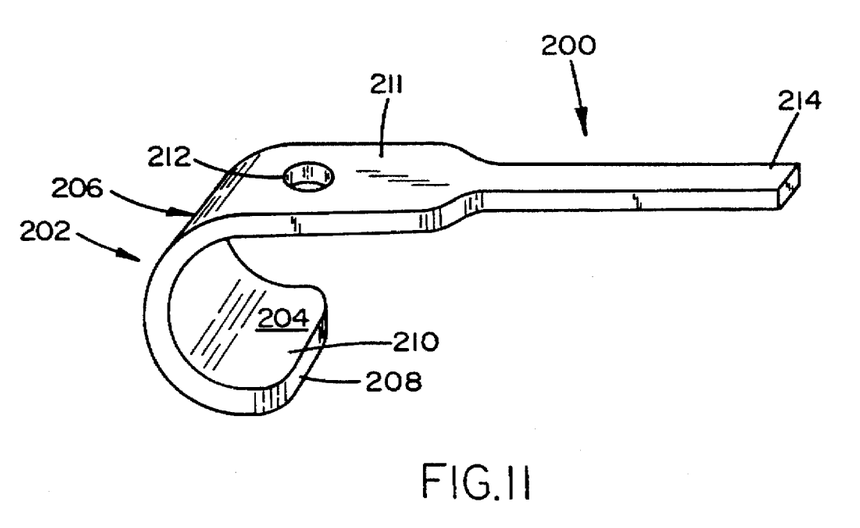
FIG. 11 is a side perspective view of an alternative first rod hooking element.

Referring now to FIG. 11, a first rod hooking element 200 of the second embodiment of the present invention is provided in a side perspective view. As with the above described embodiment, the element 200 comprises a thin and flat sheet of metal, the first end 202 of which has been curved to the shape of a hook. The hook has a semi-circular curvature defined by an inner surface 204 and an outer surface 206. The lower portion 208 of the semi-circular hook extends tangentially for a small distance, parallel to the remainder of the element. The curve is semi-circular so that it can cup and hook to the lateral outside surface of a first rod of a dual rod apparatus. The lower extending portion 208 provides addition locking surface 210 against which the rod may be compressed by a locking means described more fully below.

The top portion 211 of the first end 202 comprises a through hole 212 which is threaded and extends from a point on the top surface of the first end 202 which is to adjacent to the initial curvature of the hook portion 202 to the underside of the same. Inasmuch as a set screw (set forth with respect to FIG. 6) is to be directed therethrough to lock the element 200, and more specifically the first end 202 thereof, to a rod of the implant assembly, the through hole 212 may be angled such that the insertion and subsequent tightening of the set screw drives same toward the inner surface 204 of the hook. Such a preset angle of the through hole orientation enhances the locking strength of the set screw by increasing the cupping surface against which the rod is crushed.

The other end 214 of the rod hooking element comprises a narrowed and flat portion which has a width which is substantially reduced as compared with that of the first rod securing end 202. The thickness and corresponding structural strength of this second end 214 is, however, desirably the same as that of the rod securing end. Unlike the equivalent element 100 of the first embodiment, it is the undersurface (not shown) of this second narrowed end 214 which preferably includes a roughening, for example a diamond knurling, which provides a greater coefficient of static friction to it; this enhanced friction coefficient being desirable for the purposes of compression locking this top surface against another surface.

Figure 12:
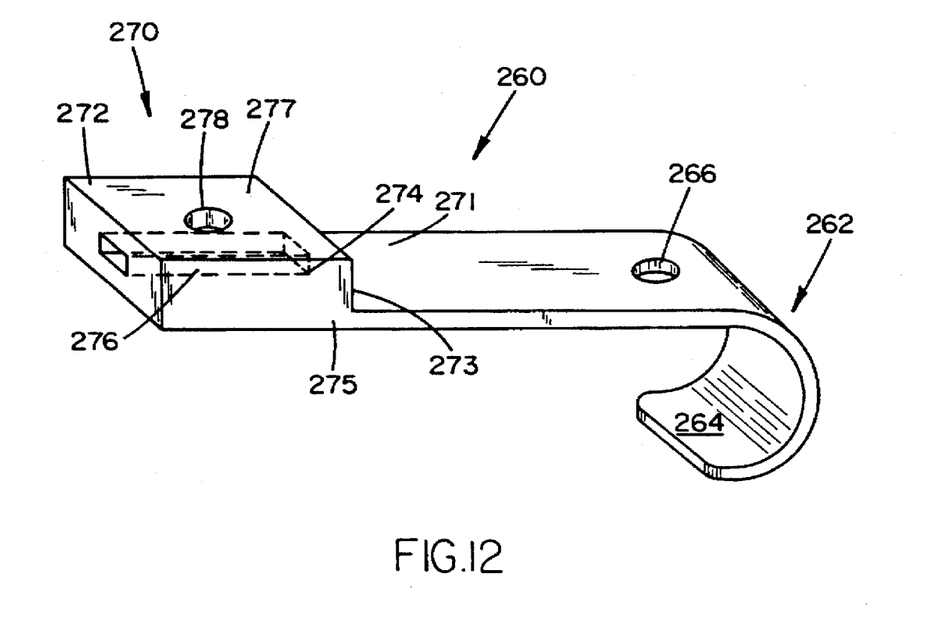
FIG. 12 is a side perspective view of an alternative second rod hooking element.

Referring now to FIG. 12, the second rod hooking element 260 of this second embodiment is provided in a side perspective view. The second element 260 includes a rod securing portion end 262 which is substantially similar to the equivalent feature of the first element 200. More specifically, the rod securing end 262 thereof has a curvate shape and an interior surface 264 for seating against lateral outside surface the second rod of the dual rod apparatus. This curvate end 262 includes a through hole 266 for receiving a set screw 120 for locking the rod to the curvate shaped end.

The other end 270 of this second rod hooking element 260 is substantially wider than the flat extending portion 214 of the first element 200, and comprises a flat extending portion 271. The extreme end 272 of this portion 271 comprises a thickened portion having lower, intermediate, and upper sections 273,274,275, respectively, integrally formed; the lower portion 273 being an integral and co-planar extension of the flat extending portion 271. The intermediate portion 274 has a flat passageway 276 therethrough which has a width and thickness which is substantially equal to the flat extending portion 214 of the first element 200 of this embodiment, and which permits the portion 214 to slide axially therein. The bottom surface of the passageway 276, which is also the top exposed surface of the lower portion 273, includes a roughening so that when the flat extending portion 214 is compressed downward thereon, the surfaces may be securely locked together.

The upper section 275 of the thickened portion includes a through hole 278 which extends from a center of the top surface 277 to the top of the passageway 276. This through hole is designed to receive a set screw 120, much like the set screws used in conjunction with the rod securing ends 202 and 262 to lock the elements 200 and 260 to their respective rods.

Figure 13:
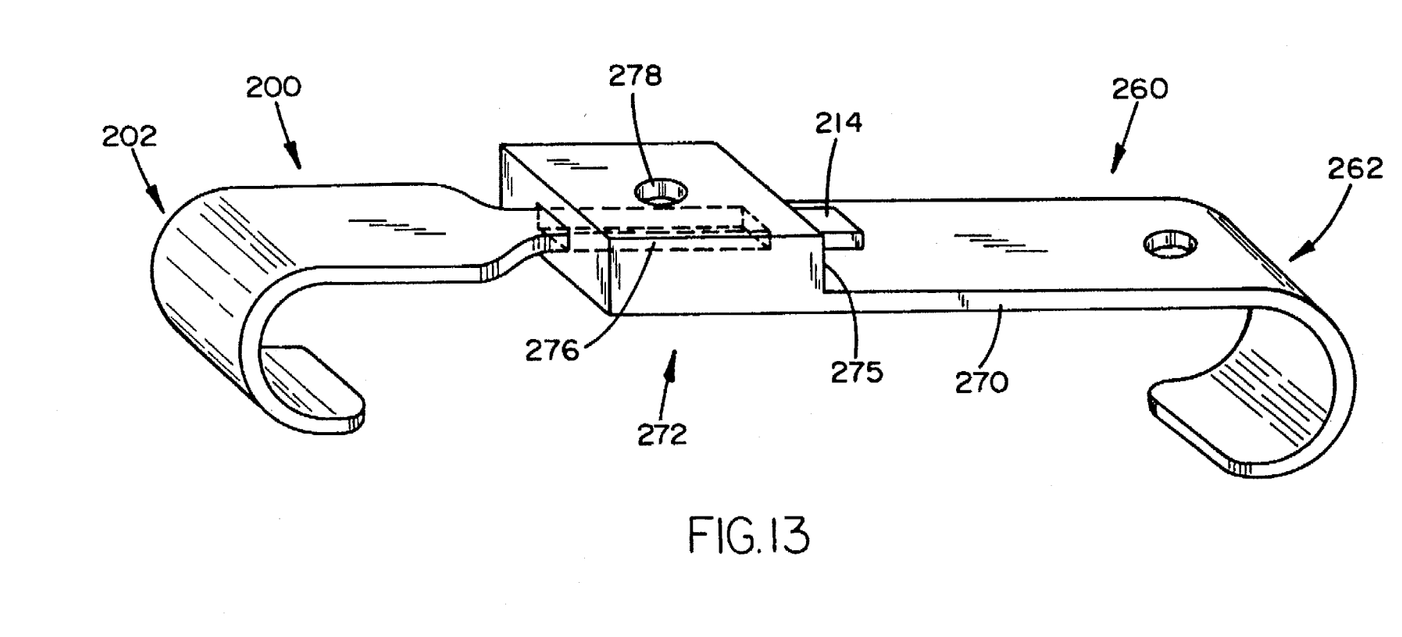
FIG. 13 is a side perspective view of a fully assembled alternative embodiment of the present invention which includes the elements illustrated in FIGS. 6, 11, and 12.

With reference now to FIG. 13, in which a fully assembled second embodiment of the present invention is provided in a side perspective view, the method of assembly and the locking of the elements is described. As with the first embodiment, the first step is to identify the proper site for the fixation of the dual rod cross-link device. The site should provide enough space along the rods for engagement of rod securing ends 202 and 262. Once this site is found, and the space separating the rods is cleared of all obstacles (for example, the spinous process) the narrow and flat extending portion 214 of the first element 200 is slidably inserted into the passageway 276 of the second end 270.

Once the flat extending portion 214 has been inserted, the rod securing ends 202 and 262 are drawn together so that the inner surfaces thereof seat against the corresponding rods. The first set screw 120 to be tightened might be the one which extends downwardly through hole 278 in the upper section 275 of the thickened end 272 and which provides the locking force onto the flat extending portion 214. The interface of the roughened surfaces provides enhanced holding strength and ensures that the elements 200 and 260 are securely coupled.

Once the length of the cross-link is been set, the other set screws 120 may be tightened down, thereby locking the element 200 and 260 to the rods themselves.

While there have been described and illustrated cross-link devices for coupling dual rods of orthopaedic apparatus together and providing enhanced stability thereto, it will be apparent to those skilled in the art that variations and modifications are possible without deviating from the broad spirit and principle of the present invention which shall be limited solely by the scope of the claims appended hereto.

We claim:

1. A variable length cross-link device for use with orthopaedic rod apparatuses having a plurality of rods, comprising:
    a first rod coupling element having first and second ends, said first end having means for coupling to a first rod, said second end comprising a narrow flat extending portion;
    a second rod coupling element having first and second ends, said first end having means for coupling to a second rod, said second end comprising a wide flat extending portion;
    top locking nut; and
    a post, said poet having a wide base, an intermediate section having a passageway which is transverse to an elongate axis the post, and a threaded upper section, such that said narrow flat extending portion of said first element may be slidably inserted into said passageway, the threaded upper section of said post may be inserted through a through hole in said wide flat extending portion of said second element,
    whereby the tightening of said top locking nut on said threaded upper section of said post causes a top surface of said narrow flat extending portion to be compression locked to a bottom surface of said wide flat extending portion.

2. The cross-link device as set forth in claim 1, wherein said top surface of said narrow flat extending portion comprises a roughened surface.

3. The cross-link device as set forth in claim 1, wherein said bottom surface of said wide flat extending portion comprises a roughened surface.

4. A variable length cross-link for use with orthopedic rod apparatuses having a plurality of rods, comprising:
    a first rod coupling element having first and second ends, said first end having means for coupling to a first rod, said second end comprising a narrow flat extending portion;
    a second rod coupling element having first and second ends, said first end having means for coupling to a second rod, said second end comprising a wide flat extending portion;
    first means for maintaining said narrow flat extending portion of said first rod coupling element in slidable relation to the wide flat extending portion of said second rod coupling element;
    second means for selectively compressing said narrow flat extending portion against said wide flat extending portion of said second rod coupling element to crush lock the two portions together;
    said first means comprising a thickened section integrally formed with said wide flat extending portion of said second element, said thickened section having a narrow flat passageway formed therein for slidably receiving said narrow flat extending portion of said first element, a top surface of said passageway having a hole; and wherein said second means comprises a set screw, insertable through said hole in said top surface for applying a compression locking force onto said narrow flat extending portion so that a bottom surface of same is crush locked to a bottom surface of said passageway.

5. The cross-link device as set forth in claim 2, wherein said roughened surface comprises a diamond knurl.

6. The cross-link device as set forth in claim 3, wherein said roughened surface comprises a diamond knurl.

7. The cross-link device as set forth in claim 4, wherein said bottom surface of said passageway is co-planar with the remainder of the wide flat extending portion.

8. The cross-link device as set forth in claim 4, wherein said bottom surface of said narrow flat extending portion comprises a roughened surface.

9. The cross-link device as set forth in claim 4, wherein said bottom surface of said passageway comprises a roughened surface.

10. The cross-link device as set forth in claim 8, wherein said roughened surface comprises a diamond knurl.

11. The cross-link device as set forth in claim 9, wherein said roughened surface comprises a diamond knurl.

12. A cross-linked dual rod orthopaedic implant apparatus comprising:
    a pair of rods disposed in a substantially parallel orientation;
    means for fixing said rods to a posterior surface of a spinal column;
    at least one variable length cross-link device for coupling said pair of rods, comprising;
    a first rod coupling element having first and second ends, said first end having means for coupling to a first rod, said second end comprising a narrow flat extending portion;
    a second rod coupling element having first and second ends, said first end having means for coupling to curved conformation with an inner surface for cupping a lateral a second rod, said second end comprising a wide flat extending portion;
    a top locking nut; and
    a post, said post having a wide base, an intermediate section having a passageway which is transverse to an elongate axis of the post, and a threaded upper section, such that said narrow flat extending portion of said first element may be slidably inserted into said passageway, the threaded upper section of said post may be inserted through the hole in said wide flat extending portion of said second element.

whereby the tightening of said to locking nut on said threaded upper section of said post causes a top surface of said narrow flat extending portion to be compression locked to a bottom surface of said wide flat extending portion.

* * * * *